(12) United States Patent
Kanigicherla et al.

(10) Patent No.: US 10,146,913 B2
(45) Date of Patent: Dec. 4, 2018

(54) PORTABLE ELECTRONIC DEVICE

(71) Applicant: INEDA SYSTEMS INC., Santa Clara, CA (US)

(72) Inventors: Balaji Kanigicherla, Hyderabad (IN); Siva Raghu Ram Voleti, Hyderabad (IN); Sagar Koorapati, Hyderabad (IN); Sarada Annapurna Gandikota, Hyderabad (IN)

(73) Assignee: Ineda Systems Pvt. Ltd, Kondapur, Cyberabad, Hyderabad (IN)

( * ) Notice: Subject to any disclaimer, the term of this patent is extended or adjusted under 35 U.S.C. 154(b) by 0 days.

(21) Appl. No.: 15/052,811

(22) Filed: Feb. 24, 2016

(65) Prior Publication Data
US 2016/0267239 A1    Sep. 15, 2016

(30) Foreign Application Priority Data
Jan. 30, 2015 (IN) .............................. 489/CHE/2015

(51) Int. Cl.
| | | |
|---|---|---|
| G08C 19/22 | (2006.01) | |
| G06F 19/00 | (2018.01) | |
| H04Q 9/00 | (2006.01) | |
| G06F 17/30 | (2006.01) | |
| G06F 9/4401 | (2018.01) | |

(52) U.S. Cl.
CPC ........ G06F 19/3418 (2013.01); G06F 9/4411 (2013.01); G06F 9/4418 (2013.01); G06F 17/30345 (2013.01); H04Q 9/00 (2013.01); H04Q 2209/40 (2013.01)

(58) Field of Classification Search
CPC ..................................................... G06F 9/4411
See application file for complete search history.

(56) References Cited

U.S. PATENT DOCUMENTS

| | | | | |
|---|---|---|---|---|
| 7,286,894 B1* | 10/2007 | Grant | ...................... | G06F 15/02 700/168 |
| 2013/0245401 A1* | 9/2013 | Estes | ................... | A61B 5/14532 600/309 |
| 2015/0099546 A1* | 4/2015 | Heo | ......................... | H04W 4/02 455/456.3 |
| 2015/0164390 A1* | 6/2015 | Larvenz | .............. | G06F 19/3406 600/365 |
| 2015/0179058 A1* | 6/2015 | Crafts | .................... | G08C 17/02 340/12.5 |

* cited by examiner

Primary Examiner — Omeed Alizada
(74) Attorney, Agent, or Firm — Workman Nydegger

(57) ABSTRACT

An Intelligent Sensor Interfacing Unit (ISIU) for detection and configuration of sensors for a Portable Electronic Device (PED). The ISIU may identify sensors connected to the PED, according to an implementation of the present subject matter. The ISIU then determines information relating to the capabilities and requirements of the identified sensors. The ISIU on the basis of the determined sensor information may access that one of the sensors' identified may be newly coupled to the PED. Further, the ISIU upon accessing that one of the sensors' may be newly coupled to the PED, shares sensor information with Host CPU of the PED. The Host CPU upon receiving such information configures the newly coupled sensor and trains the ISIU for execution of the newly coupled sensor in future.

14 Claims, 6 Drawing Sheets

PORTABLE ELECTRONIC DEVICE

CROSS-REFERENCE TO RELATED APPLICATIONS

This application claims priority to and the benefit of Indian Patent Application No. 489/CHE/2015, entitled "PORTABLE ELECTRONIC DEVICE", filed on Jan. 30, 2015, which is incorporated herein in its entirety.

TECHNICAL FIELD

The present subject matter, in general, relates to electronic devices and in particular to a portable electronic device.

BACKGROUND

With a rapid growth in communication and computing technology, computers have become faster in operation and more compact in structure. Increase in user's adaptability to new technology added with portable electronic devices' (PEDs') features like high performance, low cost and easy to carry, have made PEDs popular. In recent times, there has been an increase in the processing capabilities of the PEDs, which not only eases the day to day life, but also improves standard of living by providing various functionalities to the users.

Omnipresence of PEDs can be explained by their presence as pedometers, smart watches, smart glasses, pendants, head mounted devices, smart phones, etc., around us.

A typical PED consists of a processing unit, a memory or storage, a battery pack and sensors. The sensors interoperating with the PED help the PED to provide context-aware input/output (I/O). The sensors sense raw data and provide the raw data to the processing unit. The processing unit analyzes the raw data provided by the sensors and provides user with the contextually significant data.

PEDs support a wide range of activities requiring contextually correct data. Some of these activities can be life style management activities like counting number of steps walked, tracking sleep cycles, monitoring gap between the meals, etc. Another category of activities can be medical activity monitoring. Medical activity monitoring ranges from remote tracking of patient's vital parameters to monitoring heart rate, etc.

BRIEF DESCRIPTION OF THE FIGURES

The detailed description is described with reference to the accompanying figures. In the figures, the left-most digit(s) of a reference number identifies the figure in which the reference number first appears. The same numbers are used throughout the figures to reference like features and components. Some implementations of system and/or methods in accordance with implementations of the present subject matter are now described, by way of example only, and with reference to the accompanying figures, in which.

Figure 1:
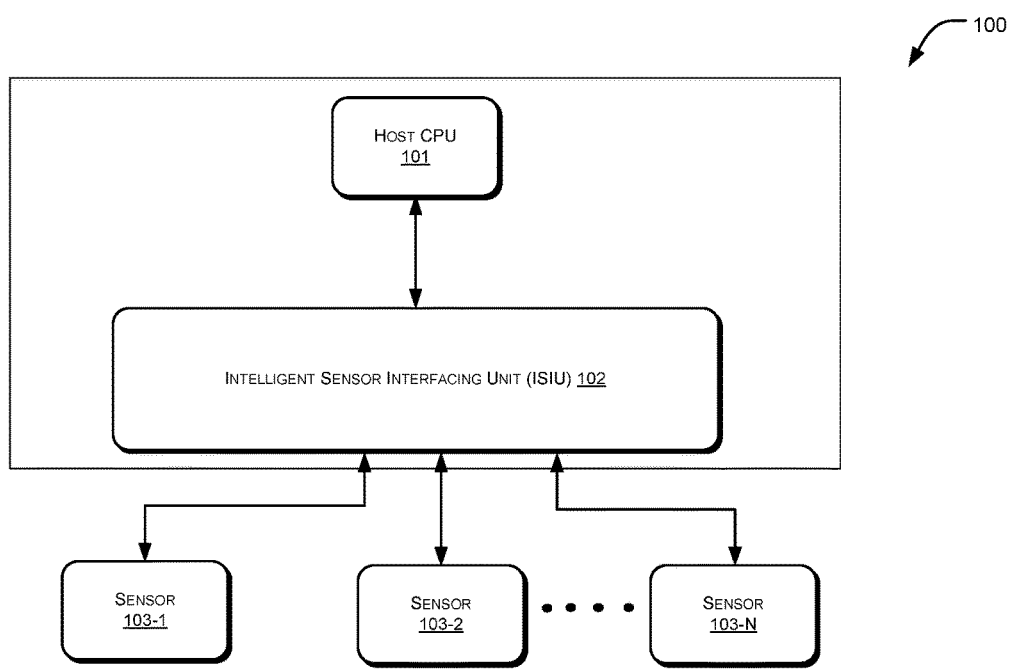
FIG. 1 illustrates a Portable Electronic Device (PED), according to an implementation of the present subject matter.

Any block diagram herein represents conceptual views of illustrative systems embodying the principles of the present subject matter. Similarly, any flow charts, flow diagrams, state transition diagrams, pseudo code, and the like represent various processes which may be substantially represented in computer readable medium and so executed by a computer or processor, whether or not such computer or processor is explicitly shown.

DETAILED DESCRIPTION

The present subject matter relates to a processing assembly of a portable electronic device (PED), including an intelligent sensor interfacing unit (ISIU) for detecting and configuring sensors. Although, the described processing assembly has been implemented in described PEDs, it would be appreciated that the processing assemblies may also be implemented in other PEDs, albeit a few variations, as would be appreciated by those skilled in the art.

In known PEDs, switching ON of a processing unit generally involves activating all components of PED, from processing unit to sensors. To control different stages of operation in the PED, such as sensing data, collection and storage of data, analysis of data, and data presentation to the user, the processing unit of the PED is first initialized. The processing unit then configures sensors connected to the PED for processing and collection of data. The process of configuration of sensors by the processing unit includes identification of the sensors, initializing the software drivers of the sensors and initialization of the sensor to start sensing data from the surrounding. Such a booting up of the processing unit amounts to wastage of power and increased initialization times.

Further, the process of configuration is carried out by the processing unit for pre-registered sensors. However, with the rapid growth in technology, new and advanced sensors can be introduced to the PED. Such, sensors are generally not pre-registered with the PED. Since, the known PEDs are configured to support only pre-registered sensors, when a sensor, not pre-registered, is introduced to the PED, the processing unit is unable to complete the process of configuration, thereby making the sensor non-operable. Hence, the users have to switch to another PED supporting such a sensor. Therefore, usability of new sensors in existing PEDs is limited and utilization of a new PED for the purpose of utilizing a new sensor is not only expensive but also inconvenient.

Certain known PEDs support a processing assembly, comprising a co-processor with the main processing unit to reduce consumption of power by the processing unit. The co-processor is configured to perform pre-data analysis on the collected data. After, the completions of the pre-data analysis, the co-processor transfers processing control to the main processing unit, to perform data analysis and data presentation to the users. However, the use of co-processors to provide preliminary processing capability occupies additional silicon area, increases silicon gate activity and consumes extra power, while the main processing unit is idle.

PEDs supporting day-to-day activities of users like heart rate monitoring consume continuous power supply for the processes of sensing data, data collection and data analysis. Undertaking such processes leads to rapid consumption of battery of the PEDs, thereby necessitating frequent charging of the battery of the PEDs. More often that not, it is practically not feasible for users on a move to charge their PEDs frequently. Attempts to increase battery capacity of the PEDs generally result in increase in size of the PEDs, thereby making them bulky and difficult to carry.

Therefore, in PEDs, a tradeoff between the processing capability and the battery life has to be made. However, market demands seldom allow such a compromise as there is a desire for PEDs that not only give high and varied processing capabilities but also last long in terms of battery life.

According to an implementation of the present subject matter, a processing assembly for a portable electronic device (PED) is described. The processing assembly may include an intelligent sensor interfacing unit (ISIU) along with the main processing unit, for detecting and configuring sensors.

In operation, the ISIU may act as an interface between sensors of the PED and a main processing unit associated with the PED. In one implementation of the present subject matter, the ISIU may initialize the sensors and modules associated with the PED, without booting the main processing unit. For example, the sensors and modules may include, but not limited to, accelerometers, gyroscope, temperature detection unit, and the like. Therefore, the main processing unit may stay in sleep or low power or hibernation mode, while the ISIU initializes the peripherals and modules associated with the PED.

During initialization of the sensors, the ISIU may detect and configure sensors connected to the PED. The detection and configuration process may include identification of at least one sensor associated with the PED followed by determination of sensor information corresponding to each of the identified sensors. In one implementation, the sensor information may indicate the capabilities and requirements of the identified sensors. For example, the sensor information may indicate power consumption of the sensor, communication protocol utilized by the sensor, and a sensor Identification (ID) associated with the sensor.

In one implementation, the ISIU may access a sensor to be new to the PED based on the gathered sensor information. That is, the sensor may not have been pre-configured by the PED and may be initialized for the first time. For instance, the PED may include 4 pre-configured sensors, corresponding to which sensor information may also be available with the ISIU. In such situation, if the ISIU, during initialization, detects 6 sensors, and correspondingly receives 6 sensor's information, the ISIU may detect 2 new sensors to be associated with the ISIU.

The ISIU, upon identification of the new sensors associated with the PED, intimates the main processing unit of the new unknown sensor detection. In operation, the ISIU may share the sensor information received from the new sensors with the main processing unit of the PED like the interface on which the sensor is detected and the associated slave address. The main processing unit of the PED may generate configuration settings for the new sensor, based on the sensor information associated with each of the new sensors. The main processing unit may also allocate a sensor ID to the new sensors upon generation of the configuration settings.

In one implementation, the main processing unit may also generate working policy for each of the new sensors. That is, the main processing unit may also define situations and circumstances in which the sensors may operate. For example, for a new analog to digital (A2D) converter sensor has been detected, the main processing unit may define a sampling rate to be used by the A2D converter under the working policy for the A2D converter.

ISIU may receive the working policy generated by the main processing unit for the new sensors and may then configure the interfacing units communicating with the sensors based on the working policy. As a result of configuring, the interfacing unit of the ISIU may populate configuration register associated with the sensors for the purpose of collecting data from the sensors and processing the collected data on the basis of the working policy.

In one implementation the ISIU may also support power management of the PED. After the configuration of the sensors the ISIU may collect data from the peripherals, and analyze the collected data. Information extracted after the analysis of the collected data may be used to trigger power management events on the basis of pre-set policies. According to another implementation of the present subject matter the power management event may correspond to booting up or waking or switching the mode of the main processing unit.

Therefore, ISIU supports peripheral detection, configuration of peripherals, data collection and analysis. Further, the ISIU boots up the main processing unit when an action is to be performed by the main processing unit, with the power management event as a trigger. The event based booting up of the main processing unit saves power, since no power is supplied to the main processing unit in idle state, hence, improving battery life.

Furthermore, in an implementation, the ISIU may be a state machine based module forming a part of the PED. Therefore, the ISIU would cover lower chip area and being a state machine based module the silicon gate activity would also be low. Additionally, smaller dimensions of the ISIU contribute trivially to the overall dimensions of the PED hence the ISIU supports the user friendly and wearable characteristics of the PED.

Also, the ISIU supports detection and configuration of pre-configured as well as new sensors connected to the PED, hence the ISIU makes PED economic, dynamic and adaptive for the user.

The manner in which the described systems and methods to achieve tradeoff between the processing capabilities and power consumption for a PED shall be implemented has been explained in details with respect to the FIG. 1-6. While aspects of described systems and methods can be implemented in any number of different computing systems, transmission environments, and/or configurations, the implementations are described in the context of the following exemplary system(s).

Portable Electronic Devices that can implement the disclosed system(s) and method(s) include, but are not limited to, a mobile phone, a wrist band, a pedometer, a head rest, a necklace, a wrist watch, an ear piece, an anklet, a finger ring, a pair of hand gloves, a pair of foot wears, a pendent, and the like.

FIG. 1 illustrates a Portable Electronic Device (PED) 100 implementing a processing assembly, with Host CPU 101 and Intelligent Sensor Interfacing Unit (ISIU) 102 as processing and pre-processing components respectively, according to an implementation of the present subject matter. In said implementation, the PED 100 communicates with a plurality of sensors 103-1, 103-2 . . . 103-N, collectively referred to as sensors 103 and individually referred to as sensor 103 hereinafter. Further, the PED 100 communicates with the sensors 103 via sensor interface part 104 (not shown in this figure) of the ISIU 102.

The Host CPU 101 may be high, medium, or low performance processor. The Host CPU 101 may be implemented as one or more microprocessors, microcomputers, microcontrollers, digital signal processors, central processing units, state machines, logic circuitries, and/or any devices that manipulate signals based on operational instructions. Among other capabilities, the Host CPU 101 may be configured to fetch and execute computer-readable instructions stored in the memory.

Further, the ISIU 102 may be a medium or low performance processor, depending on the processing capability of the Host CPU 101. The ISIU 102 is configured to provide lower processing capabilities than the Host CPU 101. The Host CPU 101 may include or may be connected to various storage controllers, like NAND flash memory, multimedia cards (MMC), Consumer Electronics Advanced Technology Attachment (CEATA), connectivity modules, such as baseband interfaces, Serial Peripheral Interfaces (SPI), Inter-integrated Circuit (I2C), and infrared data association (IrDA) compliant devices, media controllers, such as camera and integrated inter chip sound (I2S), media accelerators such as audio encode-decode engines, video encode-decode engines, and graphics accelerator, security modules such as encryption engines and key generators, communication modules such as Bluetooth, Wi-Fi, and Ethernet, universal serial bus (USB) connected devices such as pen drives and memory sticks.

The ISIU 102 may be implemented as one or more state machines, logic circuitries, and/or any devices that manipulate signals based on operational instructions. The ISIU 102 may be implemented in various types of electronic systems and is not restricted to only PEDs.

Further, the ISIU 102 may be communicating with sensors 103, like gyroscope and accelerometer. It would be appreciated that the description merely included some examples and either more, or less sensors may also be communicating with the ISIU 102.

The PED 100 may be associated with hardware resources such as, but not limited to, I/O peripherals, algorithm accelerators, storage controllers, connectivity controllers, and memory. The number and type of hardware resources may vary for different PEDs depending on user requirements, however each hardware resource may support at least on functionality of the PED 100. The hardware resources may include I/O peripherals which may either be high, medium, or low performance resources and may include, but not limited to, Inter Integrated Circuits (I2C) devices, Universal Asynchronous Receiver/Transmitter (UART) devices, Serial Peripheral Interface (SPI) devices, Integrated Inter-chip Sound (I2S) devices, Universal Serial Bus (USB) devices, Secure Digital (SD) devices and NAND devices.

The accelerators utilized in the PED 100 may include, but are not restricted to, video decoders, audio processors, etc., based on the end usage of the PED 101. The set of hardware resources may also include, the display device (not shown), but not limited to, a light emitting diode (LED) display, plasma display, liquid display, electronic paper and e-Ink display, Organic light-emitting diode (OLED) display, Active-matrix organic light-emitting diode (AMOLED) display, Thin Film Diode (TFD) display, and laser display. Further, memory (not shown) like any computer-readable medium known in the art including, for example, volatile memory, such as static random access memory (SRAM), and dynamic random access memory (DRAM), and/or non-volatile memory, such as read only memory (ROM), erasable programmable ROM, flash memories, hard disks, optical disks, and magnetic tapes may also be a part of the PED 100. Since the usage of such components is well know, the components have not been shown, and their description has also been omitted for the sake of brevity.

The ISIU 102 facilitates interaction between the Host CPU 101 and sensors 103. Further, the ISIU 102 supports detection and configuration of newly coupled sensors to the Host CPU 101, according to an implementation of the present subject matter. According to another implementation of the present subject matter, the ISIU 102 pre-analyzes the data sensed by the sensors 103 and help in power management for the PED 100. The detailed working of the ISIU 102 has been explained with respect to forthcoming figures.

Figure 2:
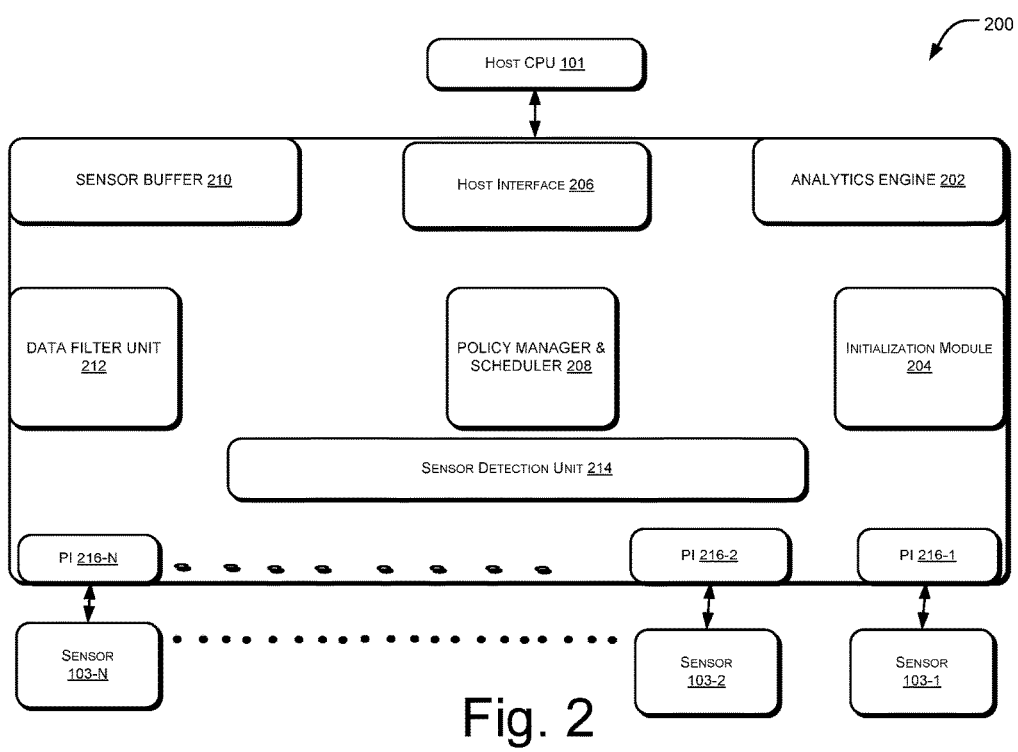
FIG. 2 schematically illustrates an architecture of the PED, in accordance with an implementation of the present subject matter.

FIG. 2 depicts modules of the ISIU 102 along with communication between the modules of ISIU 102, the Host CPU 101 and sensors 103. In other words, FIG. 2 discloses architecture of the PED 100 with ISIU 102 and sensors 103.

Peripheral Interface Controllers (PI) 216-1, 216-2 . . . 216-N embedded into the ISIU 102 are depicted, according to an implementation of the present subject matter. The PI will be collectively referred to as PIs 216 and individually referred to as PI 216 hereinafter. The PIs 216 directly interface the ISIU 102 to the sensors 103. The PIs 216 are controlled by Policy Manager and Scheduler 208, according to an implementation of the present subject matter.

According to an implementation of the present subject the Policy Manager and Scheduler 208 may access all the PIs 216 in parallel at any given point of time. The PIs 216 may be an Inter Integrated Circuits (I2C) device, Universal Asynchronous Receiver/Transmitter (UART) devices, Integrated Inter-chip Sound (I2S) devices and the likes. In an implementation of the present subject matter, the PIs 216 may be accessed by the Host CPU 101 also. The Host CPU 101 utilizes registers in Host Interface 206 to access the PIs 216.

FIG. 2 also depicts the Host Interface 206 embedded into the ISIU 102, according to an implementation of the present subject matter. The Host CPU 101 accesses the ISIU 102 and modules of the ISIU 102 through the Host Interface 206. According to an implementation of the present subject matter, the Host Interface 206 supports registers (not shown) corresponding to one or more peripheral devices of the PED. According to another implementation of the present subject matter, the registers enable the Host CPU 101 to modify any configuration or settings related functionalities of the ISIU 102, like data sensing, filtering, etc.

FIG. 2 additionally depicts the Policy Manager and Scheduler 208, as a module of the ISIU 102. The Policy Manager and Scheduler 208 may be configured to control central management of the ISIU's 102 functionalities. According to an implementation, the Policy Manager and Scheduler 208 controls communication of the ISIU 102 with the sensors. Additionally, the Policy Manager and Scheduler 208 may control the initialization of the sensors 103, according to an implementation of the present subject matter.

Further, the Policy Manager and Scheduler 208 may determine possible data analytics and interrupts associated with the sensors 103, as per an implementation of the present subject matter. Furthermore, as per another implementation of the present subject matter the Policy Manager and Scheduler 208 may be configured to sequence functions associated with the data collected from the sensors 103.

Additionally, the Policy Manager and Scheduler 208 may comprise of a timer to schedule the functions and policies for determining usage of the sensed data, according to an implementation of the present subject matter.

FIG. 2 further depicts Sensor Detection Unit 214, Initialization Module 204, Data Filter Unit 212, Analytics Engine 202, and Sensor Buffer 210 as modules of the ISIU 102.

The Sensor Detection Unit 214 may be configured to detect the type of sensors connected to the PIs 216. The Sensor Detection Unit 214 comprises of a sensor information database. According to an implementation of the present subject matter, the information database may be a Sensor Address Look UP Table (LUT). According to an implementation of the present subject matter, the LUT may be One Time Programmable (OTP). According to another implementation of the present subject matter the LUT may optionally be field programmable (based on Electrically Erasable Programmable Read-Only Memory (EEPROM) or eFuse) to configure and enable new sensors 103 communicating with the PED 100. The field programmable ability reduces the detection overhead, since only the sensors presently communicating are indicated through the LUT.

For the purpose of explanation, the LUT may include different entries for different sensors 103. Each entry may include Sensor Address, Sensor Type, and Sensor ID information. Table 1 represents an example of the LUT.

TABLE 1

| Sensor No. | Sensor Address | Sensor Type | Sensor ID |
|---|---|---|---|
| S1 | SA1 | ST1 | SID1 |
| S2 | SA2 | ST2 | SID2 |
| S3 | SA3 | ST3 | SID3 |
| . | . | . | . |
| . | . | . | . |
| . | . | . | . |
| SN | SAN | STN | SIDN |

The ISIU 102 registers unique address ID information for each sensor connected to each of the PIs 216 in the LUT. The unique address ID, representing the PI information, in combination with sensor address information is referred as Sensor Address in Table 1. For example, in case of I2C as an interface, multiple sensors may be communicating in parallel at the same time and hence, there may be multiple unique address IDs corresponding to the I2C. However, interfaces like UART communicate with only one sensor at a time; hence, there may be only one unique address ID corresponding to the UART. However, there may be multiple entries for sensor address information. It should be appreciated that the examples disclosed above are for detailed explanation only, however other implementations are also possible.

The Sensor Type is a uniquely assigned code based on the structural features and capabilities of the sensor. The Sensor Type mostly is unique for a specific vendor or manufacturer of the sensor. Further, the Sensor ID is generated by the Host CPU for a particular sensor. The Sensor ID may be used as a reference to the working policies associated with the sensor and stored in the memory.

The Sensor Detection Unit 214 after the detection of the sensors communicating with PIs 216 informs the Policy Manager and Scheduler 208. As a part of informing the Policy Manager and Scheduler 208 about the detected sensor, the Sensor Detection Unit 214 shares relevant details of the detected sensor with the Policy Manager and Scheduler 208.

Further, on the basis of the sensors detected the Policy Manager and Scheduler 208 triggers process of initializing the detected sensors. The Initialization Module 204 is used to trigger the process of initialization of the detected sensors. As a part of the process of initialization the Initialization Module 204 performs sensor register programming based on the sensor characteristics. According to an implementation of the present subject matter the Initialization Module 204 has the ability to support different sensors communicating through different PIs 216. The initialization of the sensor may be different depending on the policies associated with the sensor.

The Sensor Buffer 210 may be used by various modules of the ISIU 102 during their operations. According to an implementation of the present subject matter the Sensor Buffer 210 may be used to store the data collected from the sensors 103, performing filtering or consolidation operations and running analytics algorithms.

It should be noted that the description merely illustrates the principles of the present subject matter. It will thus be appreciated that those skilled in the art will be able to devise various arrangements that, although not explicitly described herein, embody the principles of the present subject matter and are included within its scope. Moreover, all statements herein reciting principles, aspects, and implementations of the present subject matter, as well as specific examples thereof, are intended to encompass equivalents thereof.

Figure 3:
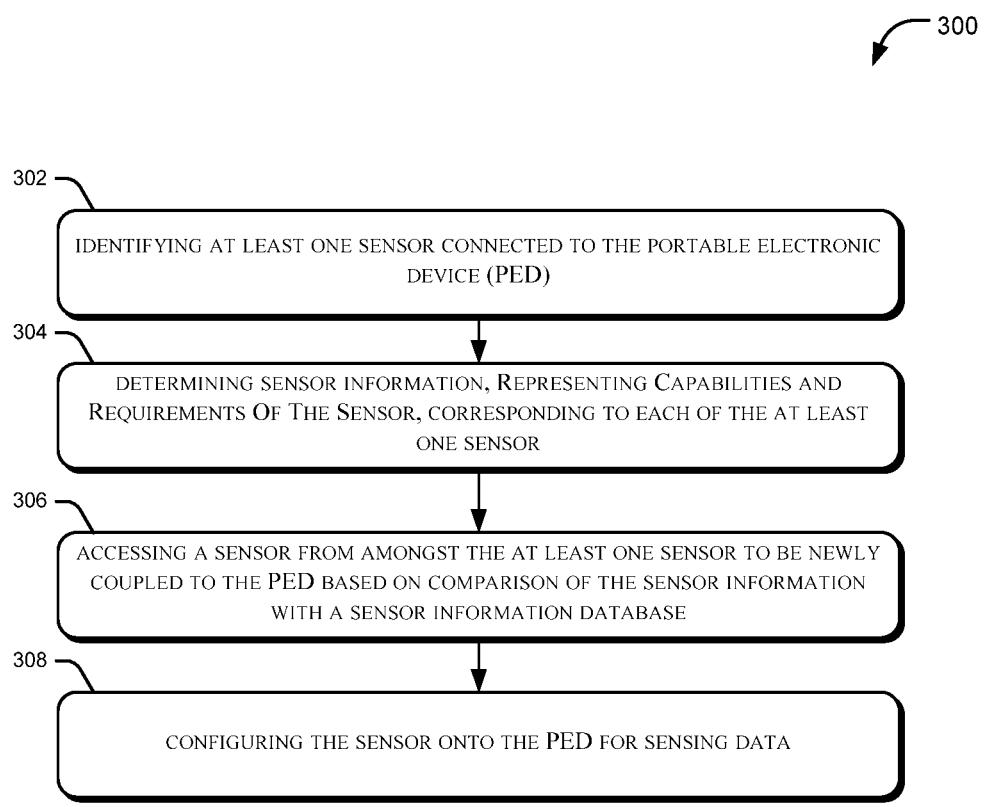
FIG. 3 illustrates a method for detection and configuration of the sensors for the PED, in accordance with an implementation of the present subject matter.

FIG. 3 illustrates a method for detection and configuration of the sensors 103 for the PED 100 by the ISIU 102 and its modules 200.

At block 302, the ISIU 102 identifies sensors connected to the PED 100 for communication. Thereafter, at block 304, the ISIU 102 identifies the sensors are connected to the PED 100, information related to the identified sensors is determined. The identified information includes sensor information corresponding to capabilities and a requirement of the sensor. The Sensor Detection Unit 214 is configured to perform the operation of sensor identification and sensor information determination. The Sensor Detection Unit 214 determines the Sensor Address, Sensor Type and Sensor ID (specified in Table 1) to determine if a pre-configured or a valid sensor is connected to the PED 100.

At block 306, the Sensor Detection Unit 214 compares the Sensor Address, Sensor Type, and Sensor ID with the corresponding entries pre-stored in the LUT for various sensors. According to an implementation of the present subject matter in a scenario of a new sensor connected to the PED 100, the Sensor Address, Sensor Type, and Sensor ID corresponding to the sensor detected by the Sensor Detection Unit 214, would not match with any corresponding entry pre-stored in the LUT for various sensors. In such a scenario the Policy Manager and Scheduler 208 informs the Host CPU 101 about the new sensor. Further, the Host CPU 101 after receiving such an information boots up and initializes the process of configuration of the new sensor, at block 308.

Figure 4:
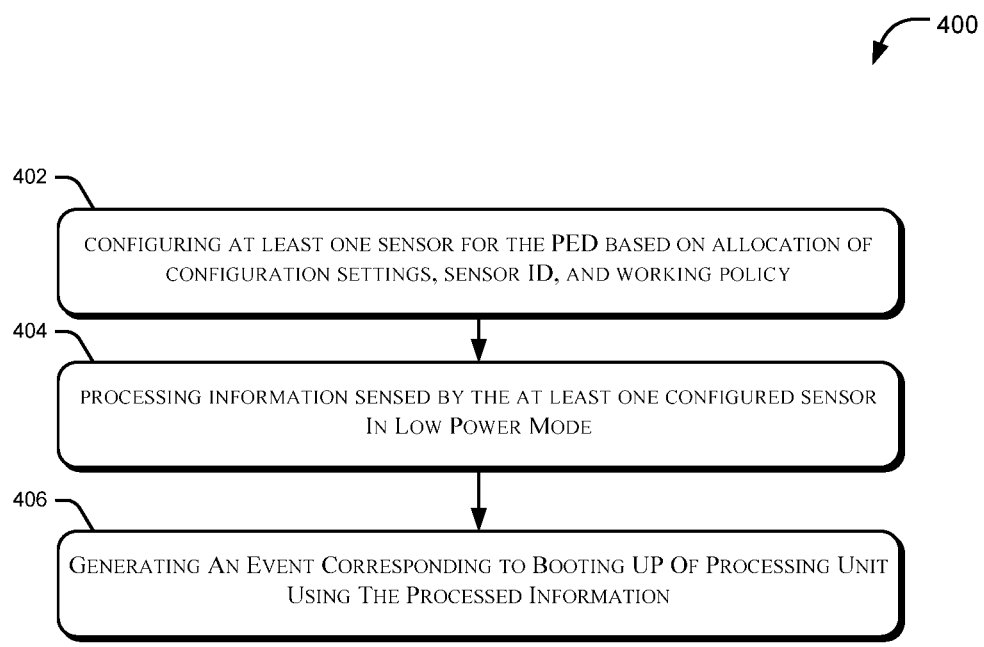
FIG. 4 illustrates a method for detection and configuring sensors for a PED, in accordance with another implementation of the present subject matter.

FIG. 4 discloses a method for detection and configuring sensors for a PED 100.

At block 402, as a part of the method for detection and configuration of sensors configuration registers, sensor details in LUT (Table 1) and execution policy or associated program code may be configured for the sensor after detection that the sensor is connected to the PED 100.

Following the configuration of the sensor the information gathered or collected or sensed, by the ISIU 102 and its corresponding modules, is processed at block 404. The processing of the sensed data is based on pre-configured or pre-defined execution policies and the program code corresponding to the sensor.

At block 406, after the processing of the data the processed data is analyzed to generate an event. The event indicates a new or unknown sensor may be connected to the PED 100, according to an implementation of the present subject matter. The event triggers the Policy Manager and Scheduler 208 to boot up the Host CPU 100, according to an implementation of the present subject matter. It would be appreciated here that the Host CPU 100 may be in low power or hibernation or power off mode before the booting up by the Policy Manager and Scheduler 208 as a trigger, according to another implementation of the present subject matter.

Figure 5:
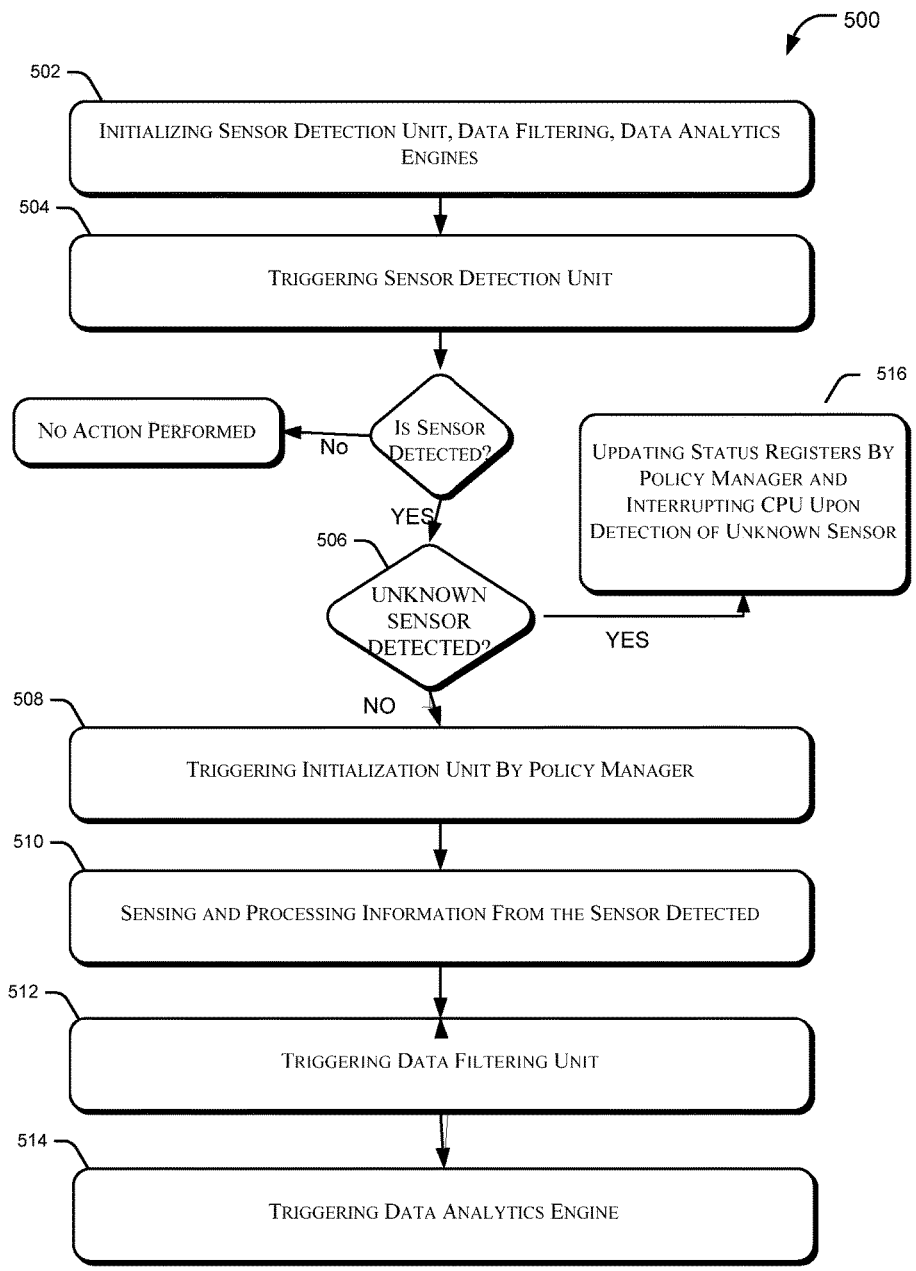
FIG. 5 illustrates a method describing the working of the Intelligent Sensor Interfacing Unit and its corresponding modules, in accordance with an implementation of the present subject matter.

FIG. 5 illustrates a method to explain the working of the ISIU 102 and its corresponding modules.

In accordance, with an implementation of the present subject matter, the ISIU 102 may be configured as a standalone sensor interfacing unit requiring zero host load by default.

At block 502, it is disclosed that during the powering on of the PED 100, the ISIU 102 powers up and initializes the Sensor detection unit 214, Initialization module 204, Policy manager and scheduler 208, Data filter unit 212, Analytics Engine 202, Host Interface 206 and sensor Buffer 210.

Further, at block 504, the ISIU 102 triggers the Sensor detection unit 214 to detect sensors connected to the PED 100 via Peripheral Interface controllers 216.

According to an implementation of the present subject matter if no sensor is detected by the sensor detection unit 214 the PED 100 enters low power mode and the processing flow stays idle or wakes up the Host CPU.

Further, at block 506, it is disclosed that after detection of the sensor connected to the PED 100, the Sensor Detection unit 214 determines if the sensor is a known or pre-configured sensor or not. The entries in the LUT (Table 1) are compared with the corresponding entries for the detected sensor to determine if operating policies and the program code corresponding to the sensor.

Block 516 discloses an implementation of the present subject matter; here in case the sensor detected is not a known sensor then the Host CPU is booted up. The details of the method adopted by the PED 100 when an unknown sensor is connected to the PED 100 would be elaborated in description of FIG. 6.

Block 508 discloses, yet another implementation of the present subject, here upon determining the sensor as a pre-configured sensor the Sensor Detection Unit 214 informs the Policy Manager and Scheduler 208. The Policy manager and Scheduler 208 triggers the Initialization Module 204 to initialize the sensor and its corresponding registers as disclosed above. At block 510, as a part of initialization of the sensors data sensed by the sensors may be collected and processed on the basis of the pre-defined program code for the sensor. Further, as disclosed at block 512 the Policy Manager and Scheduler 208 next triggers the data filter unit 212. The data filter unit 212 operates on window of samples defined as per the program code. According to an implementation of the present subject matter, there may be fixed number of samples per window. The data filter unit 212 fetches data samples from the sensors as defined by the program code. The data filter unit 212 computes certain parameters defined by the Policy Manager and scheduler 208 on the basis of the program code. Some examples of the parameters may be finding Root mean square, Mean, Fast Fourier Transfer (FFT), Signal to Noise Ratio (SNR) and the like. The data filter unit 212 next updates the Policy Manager and Scheduler 208 with the computed parameters.

Furthermore, as disclosed at block 514 the Policy Manager and Scheduler 208 initialize the Analytics Engine 202. Upon initialization the Analytics Engine 202 reads the parameters computed by the Data Filter Unit 212. The Analytics Engine 202 also reads the sensor information from the sensor buffer 210. Here, the sensor information indicates the program code, execution policies, etc., for the sensor. The sensor information comprises of activities or tasks related to the sensor. Activities or tasks may possibly be gesture pattern detection, location detection, step count, heart rate, and the likes.

The Analytics Engine 202 further computes tasks or activities mentioned above. The results of the computation of the tasks or activities are updated in the status register by the Policy Manager and Scheduler 208.

According to an implementation of the present subject matter, a power management unit (not shown) may be triggered on the basis of the status of the activity or task updated by the Policy Manager and Scheduler 208.

According to another implementation of the present subject matter, the power management unit may be configured to boot up the Host CPU 101 upon detection of a trigger.

Figure 6:
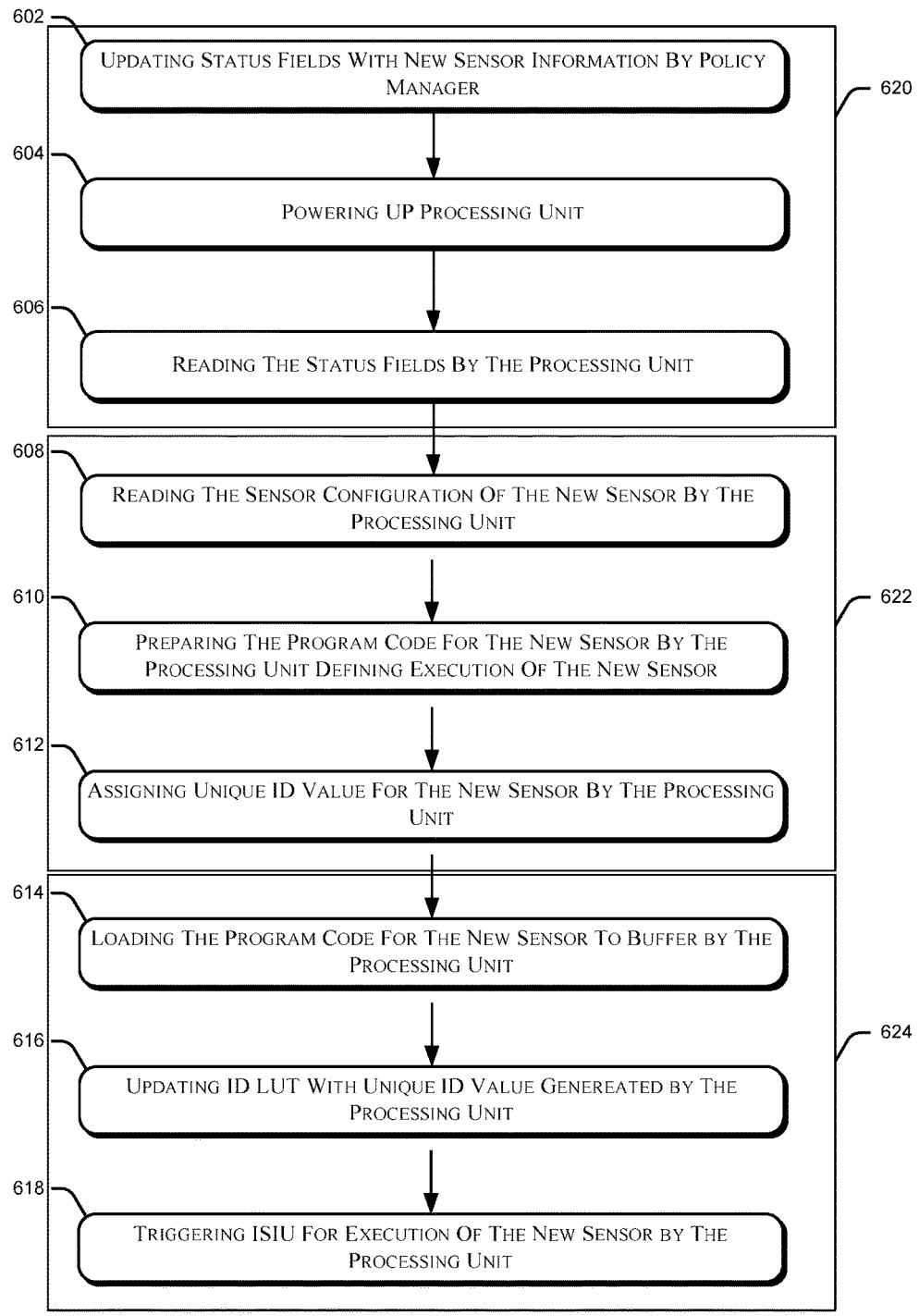
FIG. 6 illustrates a method for configuring a new sensor connected to the PED used by the ISIU in case of new sensor connected to the PED, in accordance with an implementation of the present subject matter.

FIG. 6 illustrates method used by the ISIU 102 in case of new sensor connected to the PED 100.

Upon detection of an unknown or new sensor by the Sensor Detection Unit 214, the Sensor Detection Unit 214 informs the Policy Manager and Scheduler 208 about detection of the unknown sensor.

The Policy Manager and Scheduler 208 upon receiving such an information transfers control for further processing to the Host CPU 101. As a step towards transfer of control to the Host CPU 101, booting up of the Host CPU 101 is carried out, at block 604. The Host CPU 101 stays in low power or hibernation or power off mode before the booting up by the Policy Manager and Scheduler 208 as a result of detection of the new sensor.

Further, at block 602, the Policy Manager and Scheduler 208 along with booting up the Host CPU 101, updates the status register in the Host Interface 206. The updating of the status register is an indication that the unknown sensor has been detected. The Host CPU 101 after booting up, reads the status register and further reads the configuration details of the unknown sensor, at block 606 and 608. The configuration details indicate at least the Sensor Address and Sensor type details (Table 1), in accordance with an implementation of the present subject matter. Block 620 discloses the method followed by the ISIU 102 from booting up the Host CPU 101 to reading of configuration details by the Host CPU 101. Nextafter CPU intimation, the Program Code may be prepared by the Host CPU 101. As a part of the Program Code preparation, the Host CPU 101, after reading the configuration details, goes on to read internal configuration registers, at block 608. The Host CPU 101 prepares a program code for the unknown sensor at block 610. The program code defines the capabilities and requirements of the unknown sensor. The program code further defines the functional operation and execution code and policies for the unknown sensor, according to an implementation of the present subject matter. Next the Host CPU 101 assigns a unique ID, i.e., Sensor ID (Table 1) to the unknown sensor detected, at block 612. Further, the block 622, discloses the process followed by the Host CPU for configuring new sensor.

Furthermore, block 624 discloses ISIU 102 training by the Host CPU 101 after Program Code preparation. After preparation of the program code for the unknown sensor, the Host CPU 101 loads the program code in the Sensor Buffer 210, as disclosed at block 614. The Host CPU 101 further at block 616, updates the Sensor ID for the unknown sensor in the LUT (Table 1). The updating of the Sensor ID indicates updating entry in the LUT for the unknown sensor detected. The unknown sensor as a result of presence in the LUT communicates easily like other pre-configured or known sensors connected to the PED 100. As a result of updating the LUT and loading the program code, a space in the Sensor Buffer 210 is allocated to the newly configured sensor, according to an implementation of the present subject matter.

Furthermore, at block 618 after, the configuration of the new sensor, the ISIU 102 is trained on handling operation and requirements of the new sensor by the Host CPU 101.

Once, the ISIU 102 is trained completely the execution and requirements control is transferred back to the ISIU 102 and the Host CPU 101 returns to low power or hibernation or power off mode, according to an implementation of the present subject matter.

According to an implementation of the present subject the Host CPU 101 would not be booted up in case the newly configured sensor is detected in future since the ISIU 102 has already been trained to handle the execution and requirements control for the newly configured sensor.

Although, implementations of the Intelligent Sensor Interfacing Unit have been described in language specific to structural features and/or methods, it is to be understood that the appended claims are not necessarily limited to the specific features or methods described. Rather, the specific features and methods are disclosed as exemplary implementations for utilization of the Intelligent Sensor Interfacing Unit.

We claim:

1. A method for detecting and configuring sensors for a portable electronic device (PED), the method comprising:
   identifying, by an intelligent sensor interface unit (ISIU), at least one sensor connected to the portable electronic device without triggering a processing unit of the PED, wherein the ISIU interfaces between the at least one sensor and a processing unit of the PED;
   determining, by the ISIU, sensor information corresponding to each of the at least one sensor, wherein the sensor information is indicative of capabilities and requirements of each of the at least one sensor;
   comparing, by the ISIU, the sensor information corresponding to each of the at least one sensor with a sensor information database of the PED to determine if the at least one sensor is one of a new sensor and a preconfigured sensor wherein the sensor information database includes sensor information corresponding to each of the preconfigured sensor;
   if the at least one sensor is a new sensor,
      sharing, by the ISIU, the sensor information corresponding to the at least one sensor with the processing unit;
      awaking, by the ISIU, the processing unit to define at least one of configuration settings, a sensor ID, and working policies for the at least one sensor based on the sensor information;
      receiving, by the ISIU, at least one of the configuration settings, the sensor ID, and the working policies corresponding to the at least one sensor determined to be the new sensor, from the processing unit; and
      configuring, by the ISIU, at least one of the configuration settings, the sensor ID, and the working policies for the at least one sensor determined to be the new sensor to sense and communicate data to the PED, and
   if the at least one is a preconfigured sensor,
      assessing, by the ISIU, the preconfigured sensor for sensing and communicating data to the PED based on the sensor information without triggering the processing unit.

2. The method as claimed in claim 1, wherein the method further comprises:
   updating, by the ISIU, the sensor information database with at least one of the configuration settings, sensor ID, and working policy corresponding to the at least one sensor.

3. The method as claimed in claim 1, wherein the sensor information includes at least a vendor identification ID corresponding to the at least one sensor.

4. The method as claimed in claim 1, wherein the sensor ID is a unique number associated with each of the at least one sensor of the PED, and wherein the sensor ID is allocated to each of the at least one sensor upon configuration.

5. The method as claimed in claim 1, wherein the sensor information database includes a look up table, wherein the look up table includes at least the sensor information and a sensor ID corresponding to each of the preconfigured sensor.

6. The method as claimed in claim 1, further comprises scheduling at least one sensor event based on the configured sensor.

7. An Intelligent Sensor Interfacing Unit (ISIU) for detecting and configuring sensors for a Portable electronic Device (PED), the ISIU comprises of:
   a sensor detection unit to:
      identify at least one sensor connected to the PED without triggering a processing unit of the PED, wherein the ISIU interfaces between the at least one sensor and a processing unit of the PED;
      determine sensor information corresponding to each of the at least one sensor, wherein the sensor information is indicative of capabilities and requirements of each of the at least one sensor;
      compare the sensor information corresponding to each of the at least one sensor with a sensor information database of the PED to determine if the at least one sensor is one of a new sensor and a preconfigured sensor, wherein the sensor information database includes sensor information corresponding to each of the preconfigured sensor;
   if the at least one sensor is a new sensor,
      the sensor detection unit is to:
         share the sensor information corresponding to the at least one sensor with the processing unit of the PED;
         awake the processing unit to define at least one of configuration settings, a sensor ID, and working policies for the at least one sensor based on the sensor information; and
      a policy manager and scheduler to:
         receive at least one of the configuration settings, the sensor ID, and the working policies corresponding to the at least one sensor determined to be the new sensor from the processing unit; and configure at least one of the configuration settings, the sensor ID, and the working policies for the at least one sensor determined to be new sensor to sense and communicate data with the PED, and if the at least one is a preconfigured sensor,
the sensor detection unit is to:
assess the preconfigured sensor for sensing and communicating data to the PED based on the sensor information without triggering the processing unit.

8. The ISIU as claimed in claim 7, wherein the sensor information includes at least a vendor identification ID corresponding to the at least one sensor.

9. The ISIU as claimed in claim 7, wherein the sensor ID is a unique number associated with each of the at least one sensor of the PED, and wherein the sensor ID is allocated to each of the at least one sensor upon configuration by the policy manager and scheduler.

10. The ISIU as claimed in claim 7, further schedules at least one sensor event based on the configured sensor.

11. A portable electronic device (PED) for detecting and configuring sensors, the PED comprising:
a host Central Processing Unit (CPU) to:
identify at least one sensor connected to the PED, without triggering a processing unit of the PED, wherein the ISIU interfaces between the at least one sensor and a processing unit of the PED;
determine sensor information corresponding to each of the at least one sensor, wherein the sensor information is indicative of capabilities and requirements of each of the at least one sensor;
compare the sensor information corresponding to each of the at least one sensor with a sensor information database of the PED to determine if the at least one sensor is one of a new sensor and a preconfigured sensor, wherein the sensor information database includes sensor information corresponding to each of the preconfigured sensor;

if the at least one sensor is a new sensor,
the host Central Processing Unit (CPU) is to:
share the sensor information corresponding to the at least one sensor with the processing unit of the PED;
awake the processing unit to define at least one of configuration settings, a sensor ID, and working policies for the at least one sensor based on the sensor information;
receive at least one of the configuration settings, the sensor ID, and the working policies corresponding to the at least one sensor determined to be the new sensor from the processing unit; and
configure at least one of the configuration settings, the sensor ID, and the working policies for the at least one sensor determined to be new sensor to sense and communicate data to the PED; and if the at least one is a preconfigured sensor,
the host Central Processing Unit (CPU) is to:
assess the preconfigured sensor for sensing and communicating data to the PED based on the sensor information without triggering the processing unit.

12. The PED as claimed in claim 11, wherein host CPU is further configured to:
update the sensor information database with at least one of the configuration settings, sensor ID, and working policy corresponding to the at least one sensor.

13. The PED as claimed in claim 11, wherein the Host CPU comprises of host interface registers to interface with an Intelligent Sensor Interfacing Unit (ISIU) which further handles data sampling, filtering, analytics of the sensed data while the Host CPU goes to low power mode.

14. The PED as claimed in claim 13, wherein the Host CPU is configured to enable the ISIU through the host interface register, to sense and communicate data from the at least one sensor.

* * * * *